United States Patent [19]
Munroe et al.

[11] Patent Number: 6,020,158
[45] Date of Patent: Feb. 1, 2000

[54] ISOLATED POLYNUCLEOTIDE FOR NOVEL G-PROTEIN COUPLED RECEPTOR

[75] Inventors: Donald G. Munroe, Waterdown; Tejal B. Vyas, Mississauga, both of Canada

[73] Assignee: Allelix Biopharmaceuticals, Inc., Ontario, Canada

[21] Appl. No.: 08/861,747

[22] Filed: May 22, 1997

[51] Int. Cl.$^7$ .......................... C07H 21/04; C12N 15/00; C12P 21/04

[52] U.S. Cl. ........................ 435/69.1; 435/70.1; 435/71.1; 435/320.1; 435/325; 435/252.3; 435/254.11; 536/23.5; 935/11; 935/22; 935/66

[58] Field of Search .................................. 536/23.5, 23.1; 435/320.1, 325, 69.1, 70.1, 71.1, 252.3, 254.11; 935/11, 22, 66

[56] References Cited

FOREIGN PATENT DOCUMENTS 9630406  10/1996  WIPO.

OTHER PUBLICATIONS

Mills et al, Cancer Research 48, 1066–1071, Mar. 1, 1988, A Putative New Growth Factor in Ascitic Fluid from Ovarian Cancer Patients: Identification . . . .

Moolenaar et al, Rev. Physio. Biochem. Pharmacol., vol. 119, 192, 47–169, Lysophosphatidic Acid: A Bioactive Phspholipid with Growth Factor–Like Properties.

Chun et al, Molecular and Cellular Neuroscience, 7, 304–321 (1996), Clonal Cell Lines Produced by Infection of Neocortical Neuroblasts Using Multiple Oncogenes Transduced . . . .

Hla et al, The Journal of Biological Chemistry, vol. 265, No. 16, pp. 9308–9313, An Abundant Transcript Induced in Differentiating Human Endothelial Cells Encodes . . . .

Xu et al, Journal of Cellular Physiology, 163:441–450 (1995), Effect of Lysophospholipids on Signaling in the Human Jurkat T Cell Line.

Postma et al, Abstract, Issue 1:1996, vol. 15, Jan.–Dec. 1996, Serum–Induced Membrane Depolarization in Quiescent Fibroblats:Activation of a Chloride . . . .

Yuan et al, The Journal of Biological Chemistry, vol. 271, No. 43, pp. 27090–27098, The Bioactive Phospholipid, Lysophosphatidylcholine, Induces Cellular Effects . . . .

Guo et al, Proc. Natl. Acad. Sci. USA 93, (1996) 14367–14371, Molecular cloning of a high–affinity receptor for the growth factor–like lipid mediator lysophosphatidic acid . . . .

Thomson et al, Molecular Pharmacology, 45, 718–723, Identification and Characterization of a Lysophosphatidic Acid Receptor.

Hiller et al, GenBank Database No. AA419064, May 19, 1997.

Adams et al GenBank Database No. AA298791, Apr. 18, 1997.

Hillier et al GenBank Database No. AA419092; May 19, 1997.

Khan et al. GenBank Database No. T02954; 1992.

Hillier et al GenBank Database No. W60555; Nov. 25, 1996.

Adams et al GenBank Database No. AA312795; Apr. 19, 1997.

GenBank Accession No. W60555, Hillier et al, publically available Nov. 25, 1996.

Gura et al., Science. 270:575–577, 1995.

Jazin et al., Regulatory Peptides, 47:247–258, 1993.

Herzog et al, DNA & Cell Biology, 12 (6): 465–471, 1993.

Stein et al., Science 261:1004–1012, 1993.

Lazar et al, Molecular and Cellular Biology Mar. 1998, 8(3):1247–1252.

Burgess et al, The Journal of Cell Biology, 111:2129–2138, 1990.

Rudirger, J. in "Peptide Hormones", University Park Press, Baltimore, Jun. 1976 pp. 1–7.

*Primary Examiner*—Patricia A. Duffy
*Attorney, Agent, or Firm*—Nikaido Marmelstein Murray & Oram, LLP.

[57] ABSTRACT

The present invention is directed to an isolated polynucleotide for novel G-Protein Coupled Receptors. More particularly, the present invention provides an isolated polynucleotide comprising the nucleic acid sequence SEQ ID NO: 1 or nucleic acid sequences that hybridize to SEQ ID NO: 1 or its complimentary strand having at least 40% sequence identity. Preferably, the hybridizing nucleic acid sequence should hybridize under stringent conditions and in particular have 85% sequence identity, more preferably 90% sequence identity, and most preferably 95% sequence identity.

8 Claims, 7 Drawing Sheets

Fig. 1A

```
              CGCTCCCGCCGCAGTCGCCGGGCCATGGGCCTCGAGCCCGCCCCGAACCCCCGCGAGCCC    SEQ ID NO: 1
              GCGAGGGCGGCGTCAGCGGCCCGGTACCCGGAGCTCGGGCGGGGCTTGGGGGCGCTCGGG
    1         ---------+---------+---------+---------+---------+---------+    60

M  V  I  M  G  Q  C  Y  Y  N   SEQ ID NO:2
              GCCTTGTCTGCGGCGTGACTGGAGGCCCAGATGGTCATCATGGGCCAGTGCTACTACAAC
              CGGAACAGACGCCGCACTGACCTCCGGGTCTACCAGTAGTACCCGGTCACGATGATGTTG
   61         ---------+---------+---------+---------+---------+---------+   120

E  T  I  G  F  F  Y  N  N  S  G  K  E  L  S  S  H  W  R  P
              GAGACCATCGGTTTCTTCTATAACAACAGTGGCAAAGAGCTCAGCTCCCACTGGCGGCCC
              CTCTGGTAGCCAAAGAAGATATTGTTGTCACCGTTTCTCGAGTCGAGGGTGACCGCCGGG
  121         ---------+---------+---------+---------+---------+---------+   180

K  D  V  V  V  V  A  L  G  L  T  V  S  V  L  V  L  L  T  N
              AAGGATGTGGTCGTGGTGGCACTGGGGCTGACCGTCAGCGTGCTGGTGCTGCTGACCAAT
              TTCCTACACCAGCACCACCGTGACCCCGACTGGCAGTCGCACGACCACGACGACTGGTTA
  181         ---------+---------+---------+---------+---------+---------+   240

L  L  V  I  A  A  I  A  S  N  R  R  F  H  Q  P  I  Y  Y  L
              CTGCTGGTCATAGCAGCCATCGCCTCCAACCGCCGCTTCCACCAGCCCATCTACTACCTG
              GACGACCAGTATCGTCGGTAGCGGAGGTTGGCGGCGAAGGTGGTCGGGTAGATGATGGAC
  241         ---------+---------+---------+---------+---------+---------+   300

L  G  N  L  A  A  A  D  L  F  A  G  V  A  Y  L  F  L  M  F
              CTCGGCAATCTGGCCGCGGCTGACCTCTTCGCGGGCGTGGCCTACCTCTTCCTCATGTTC
              GAGCCGTTAGACCGGCGCCGACTGGAGAAGCGCCCGCACCGGATGGAGAAGGAGTACAAG
  301         ---------+---------+---------+---------+---------+---------+   360
```

Fig. 1B

```
              H  T  G  P  R  T  A  R  L  S  L  E  G  W  F  L  R  Q  G  L
      CACACTGGTCCCCGCACAGCCCGACTTTCACTTGAGGGCTGGTTCCTGCGGCAGGGCTTG
      GTGTGACCAGGGGCGTGTCGGGCTGAAAGTGAACTCCCGACCAAGGACGCCGTCCCGAAC
361   ---------+---------+---------+---------+---------+---------+   420

L  D  T  S  L  T  A  S  V  A  T  L  L  A  I  A  V  E  R  H
      CTGGACACAAGCCTCACTGCGTCGGTGGCCACACTGCTGGCCATCGCCGTGGAACGGCAC
      GACCTGTGTTCGGAGTGACGCAGCCACCGGTGTGACGACCGGTAGCGGCACCTTGCCGTG
421   ---------+---------+---------+---------+---------+---------+   480

R  S  V  M  A  V  Q  L  H  S  R  L  P  R  G  R  V  V  M  L
      CGCAGTGTGATGGCCGTACAGTTGCACAGCCGCCTGCCCCGTGGCCGCGTGGTCATGCTC
      GCGTCACACTACCGGCATGTCAACGTGTCGGCGGACGGGGCACCGGCGCACCAGTACGAG
481   ---------+---------+---------+---------+---------+---------+   540

I  V  G  V  W  V  A  A  L  G  L  G  L  L  P  A  H  S  W  H
      ATTGTGGGCGTGTGGGTGGCTGCCCTGGGCCTGGGGCTGTTGCCTGCCCACTCCTGGCAC
      TAACACCCGCACACCCACCGACGGGACCCGGACCCCGACAACGGACGGGTGAGGACCGTG
541   ---------+---------+---------+---------+---------+---------+   600

C  L  C  A  L  D  R  C  S  R  M  A  P  L  L  S  R  S  Y  L
      TGCCTCTGTGCCCTGGACCGCTGCTCACGCATGGCACCCCTGCTCAGCCGCTCCTATTTG
      ACGGAGACACGGGACCTGGCGACGAGTGCGTACCGTGGGGACGAGTCGGCGAGGATAAAC
601   ---------+---------+---------+---------+---------+---------+   660

A  V  W  A  L  S  S  L  L  V  F  L  L  M  V  A  V  Y  T  R
      GCCGTCTGGGCTCTGTCGAGCCTGCTTGTCTTCCTGCTCATGGTGGCTGTGTACACCCGC
      CGGCAGACCCGAGACAGCTCGGACGAACAGAAGGACGAGTACCACCGACACATGTGGGCG
661   ---------+---------+---------+---------+---------+---------+   720

I  F  L  Y  V  R  R  R  V  Q  R  M  A  E  H  V  S  C  H  P
      ATTTTTTTATACGTGCGGCGGCGAGTGCAGCGCATGGCAGAGCATGTCAGCTGCCACCCC
      TAAAAAAATATGCACGCCGCCGCTCACGTCGCGTACCGTCTCGTACAGTCGACGGTGGGG
721   ---------+---------+---------+---------+---------+---------+   780
```

Fig. 1C

```
              R  Y  R  E  T  T  L  S  L  V  K  T  V  V  I  I  L  G  A  F
           CGCTACCGAGAGACCACGCTCAGCCTGGTCAAGACTGTTGTCATCATCCTGGGGGCGTTC
           GCGATGGCTCTCTGGTGCGAGTCGGACCAGTTCTGACAACAGTAGTAGGACCCCCGCAAG
     781   ---------+---------+---------+---------+---------+---------+  840

V  V  C  W  T  P  G  Q  V  V  L  L  L  D  G  L  G  C  E  S
           GTGGTCTGCTGGACACCAGGCCAGGTGGTACTGCTCCTGGATGGTTTAGGCTGTGAGTCC
           CACCAGACGACCTGTGGTCCGGTCCACCATGACGAGGACCTACCAAATCCGACACTCAGG
     841   ---------+---------+---------+---------+---------+---------+  900

C  N  V  L  A  V  E  K  Y  F  L  L  L  A  E  A  N  S  L  V
           TGCAATGTCCTGGCTGTAGAAAAGTACTTCCTACTGTTGGCCGAGGCCAACTCACTGGTC
           ACGTTACAGGACCGACATCTTTTCATGAAGGATGACAACCGGCTCCGGTTGAGTGACCAG
     901   ---------+---------+---------+---------+---------+---------+  960

N  A  A  V  Y  S  C  R  D  A  E  M  R  R  T  F  R  R  L  L
           AATGCTGCTGTGTACTCTTGCCGAGATGCTGAGATGCGCCGCACCTTCCGCCGCCTTCTC
           TTACGACGACACATGAGAACGGCTCTACGACTCTACGCGGCGTGGAAGGCGGCGGAAGAG
     961   ---------+---------+---------+---------+---------+---------+
    1020

C  C  A  C  L  R  Q  P  T  R  E  S  V  H  Y  T  S  S  A  Q
           TGCTGCGCGTGCCTCCGCCAGCCCACCCGCGAGTCTGTCCACTATACATCCTCTGCCCAG
           ACGACGCGCACGGAGGCGGTCGGGTGGGCGCTCAGACAGGTGATATGTAGGAGACGGGTC
    1021   ---------+---------+---------+---------+---------+---------+
    1080

G  G  A  S  T  R  I  M  L  P  E  N  G  H  P  L  M  D  S  T
           GGAGGTGCCAGCACTCGCATCATGCTTCCCGAGAACGGCCACCCACTGATGGACTCCACC
           CCTCCACGGTCGTGAGCGTAGTACGAAGGGCTCTTGCCGGTGGGTGACTACCTGAGGTGG
    1081   ---------+---------+---------+---------+---------+---------+
    1140

L  *
           CTTTAGCTACCTTGAACTTCAGCGGTACGCGGCAAGCAACAAATCCACAGCCCCTGATGA
```

Fig. 1D

```
     GAAATCGATGGAACTTGAAGTCGCCATGCGCCGTTCGTTGTTTAGGTGTCGGGGACTACT
1141 ---------+---------+---------+---------+---------+---------+
1200

CTTGTGGGTGCTCCTGGCTCAACCCAACCAACAGGACTGACTGACCGGCAGGACAAGGTC
     GAACACCCACGAGGACCGAGTTGGGTTGGTTGTCCTGACTGACTGGCCGTCCTGTTCCAG
1201 ---------+---------+---------+---------+---------+---------+
1260

TGGCATGGCACAGCACCACTGCCAGGCCTCCCCAGGCACACCACTCTGCCCAGGGAATGG
     ACCGTACCGTGTCGTGGTGACGGTCCGGAGGGGTCCGTGTGGTGAGACGGGTCCCTTACC
1261 ---------+---------+---------+---------+---------+---------+
1320

GGGCTTTGGGTCATCTCCCACTGCCTGGGGGAGTCAGATGGGGTGCAGGAATCTGGCTCT
     CCCGAAACCCAGTAGAGGGTGACGGACCCCCTCAGTCTACCCCACGTCCTTAGACCGAGA
1321 ---------+---------+---------+---------+---------+---------+
1380

TCAGCCATCCCAGGTTTAGGGGGTTTGTAACAGACATTATTCTGTTTTCACTGCGTATCC
     AGTCGGTAGGGTCCAAATCCCCCAAACATTGTCTGTAATAAGACAAAAGTGACGCATAGG
1381 ---------+---------+---------+---------+---------+---------+
1440

TTGGTAAGCCCTGTGGACTGGTTCCTGCTGTGTGATGCTGAGGGTTTTAAGGTGGGGAGA
     AACCATTCGGGACACCTGACCAAGGACGACACACTACGACTCCCAAAATTCCACCCCTCT
1441 ---------+---------+---------+---------+---------+---------+
1500

GATAAGGGCTCTCTCGGGCCATGCTACCCGGTATGACTGGGTAATGAGGACAGACTGTGG
     CTATTCCCGAGAGAGCCCGGTACGATGGGCCATACTGACCCATTACTCCTGTCTGACACC
1501 ---------+---------+---------+---------+---------+---------+
1560
```

```
              ACACCCCATYTACCTGAGTCTGATTCTTTAGCAGCAGAGACTGAGGGGTGCAGAGTGTGA
              TGTGGGGTARATGGACTCAGACTAAGAAATCGTCGTCTCTGACTCCCCACGTCTCACACT
      1561    ---------+---------+---------+---------+---------+---------+
      1620

GCTGGGAAAGGTTTGTGGCTCCTTGCAGCCTCCAGGGACTGGCCTGTCCCCGATAGAATT
              CGACCCTTTCCAAACACCGAGGAACGTCGGAGGTCCCTGACCGGACAGGGGCTATCTTAA
      1621    ---------+---------+---------+---------+---------+---------+
      1680

GAAGCAGTCCACGGGGAGGGGATGATACAAGGAGTAAACCTTTCTTTACACTCTGAGGTC
              CTTCGTCAGGTGCCCCTCCCCTACTATGTTCCTCATTTGGAAAGAAATGTGAGACTCCAG
      1681    ---------+---------+---------+---------+---------+---------+
      1740

TCCAAAACATTTGTTGTTATC
              AGGTTTTGTAAACAACAATAG
      1741    ---------+---------+-   1761
```

```
     TTACGAATTAATACGATCACTATAGGGAGACCAAGCTTGGTACCGAGCTCGGATCCACTA        SEQ ID NO:3
1    ---------+---------+---------+---------+---------+---------+   60
     GTAACGGCCGCCAGTGTGGGGAATTCCGCTCCCGCCGCAGTCGCCGGGCCATGGGCCTCG
61   ---------+---------+---------+---------+---------+---------+   120
     AGCCCGCCCCGAACCCCCGCGAGCCCGCCTTGTCTGCGGCGTGACTGGAGGCCCAGATGG
121  ---------+---------+---------+---------+---------+---------+   180
     TCATCATGGGCCAGTGCTACTACAACGAGACCATCGGTTTCTTCTATAACAACAGTGGCA
181  ---------+---------+---------+---------+---------+---------+   240
     AAGAGCTCAGCTCCCACTGGCGGCCCAAGGATGTGGTCGTGGTGGCACTGGGGCTGACCG
241  ---------+---------+---------+---------+---------+---------+   300
     TCAGCGTGCTGGTGCTGCTGACCAATCTGCTGGTCATAGCAGCCATCGCCTCCAACCGCC
301  ---------+---------+---------+---------+---------+---------+   360
     GCTTCCACCAGCCCATCTACTACCTGCTCGGCAATCTGGCCGCGGCTGACCTCTTCGCGG
361  ---------+---------+---------+---------+---------+---------+   420
     GCGTGGCCTACCTCTTCCTCATGTTCCACACTGGTCCCCGCACAGCCCGACTTTCACTTG
421  ---------+---------+---------+---------+---------+---------+   480
     AGGGCTGGTTCCTGCGGCAGGGCTTGCTGGACACAAGCCTCACTGCGTCGGTGGCCACAC
481  ---------+---------+---------+---------+---------+---------+   540
     TGCTGGCCATCGCCGTGGAACGGCACCGCAGTGTGATGGCCGTACAGTTGCACAGCCGCC
541  ---------+---------+---------+---------+---------+---------+   600
     TGCCCCGTGGCCGCGTGGTCATGCTCATTGTGGGCGTGTGGGTGGCTGCCCTGGGCCTGG
601  ---------+---------+---------+---------+---------+---------+   660
     GGCTGTTGCCTGCCCACTCCTGGCACTGCCTCTGTGCCCTGGACCGCTGCTCACGCATGG
661  ---------+---------+---------+---------+---------+---------+   720
     CACCCCTGCTCAGCCGCTCCTATTTGGCCGTCTGGGCTCTGTCGAGCCTGCTTGTCTTCC
721  ---------+---------+---------+---------+---------+---------+   780
     TGCTCATGGTGGCTGTGTACACCCGCATTTTTTTATACGTGCGGCGGCGAGTGCAGCGCA
781  ---------+---------+---------+---------+---------+---------+   840
     TGGCAGAGCATGTCAGCTGCCACCCCCGCTACCGAGAGACCACGCTCAGCCTGGTCAAGA
841  ---------+---------+---------+---------+---------+---------+   900
     CTGTTGTCATCATCCTGGGGGCGTTCGTGGTCTGCTGGACACCAGGCCAGGTGGTACTGC
901  ---------+---------+---------+---------+---------+---------+   960
     TCCTGGATGGTTTAGGCTGTGAGTCCTGCAATGTCCTGGCTGTAGAAAAGTACTTCCTAC
961  ---------+---------+---------+---------+---------+---------+   1020
     TGTTGGCCGAGGCCAACTCACTGGTCAATGCTGCTGTGTACTCTTGCCGAGATGCTGAGA
1021 ---------+---------+---------+---------+---------+---------+   1080
     TGCGCCGCACCTTCCGCCGCCTTCTCTGCTGCGCGTGCCTCCGCCAGCCCACCCGCGAGT
1081 ---------+---------+---------+---------+---------+---------+   1140
     CTGTCCACTATACATCCTCTGCCCAGGGAGGTGCCAGCACTCGCATCATGCTTCCCGAGA
1141 ---------+---------+---------+---------+---------+---------+   1200
     ACGGCCACCCACTGATGGACTCCACCCTTTAGCTACCTTGAACTTCAGCGGTACGCGGCA
1201 ---------+---------+---------+---------+---------+---------+   1260
```

```
      AGCAACAAATCCACAGCCCCTGATGACTTGTGGGTGCTCCTGGCTCAACCCAACCAACAG
1261  ---------+---------+---------+---------+---------+---------+  1320

GACTGACTGACCGGCAGGACAAGGTCTGGCATGGCACAGCACCACTGCCAGGCCTCCCCA
1321  ---------+---------+---------+---------+---------+---------+  1380

GGCACACCACTCTGCCCAGGGAATGGGGGCTTTGGGTCATCTCCCACTGCCTGGGGGAGT
1381  ---------+---------+---------+---------+---------+---------+  1440

CAGATGGGGTGCAGGAATCTGGCTCTTCAGCCATCCCAGGTTTAGGGGGTTTGTAACAGA
1441  ---------+---------+---------+---------+---------+---------+  1500

CATTATTCTGTTTTCACTGCGTATCCTTGGTAAGCCCTGTGGACTGGTTCCTGCTGTGTG
1501  ---------+---------+---------+---------+---------+---------+  1560

ATGCTGAGGGTTTTAAGGTGGGGAGAGATAAGGGCTCTCTCGGGCCATGCTACCCGGTAT
1561  ---------+---------+---------+---------+---------+---------+  1620

GACTGGGTAATGAGGACAGACTGTGGACACCCCATYTACCTGAGTCTGATTCTTTAGCAG
1621  ---------+---------+---------+---------+---------+---------+  1680

CAGAGACTGAGGGGTGCAGAGTGTGAGCTGGGAAAGGTTTGTGGCTCCTTGCAGCCTCCA
1681  ---------+---------+---------+---------+---------+---------+  1740

GGGACTGGCCTGTCCCCGATAGAATTGAAGCAGTCCACGGGGAGGGGATGATACAAGGAG
1741  ---------+---------+---------+---------+---------+---------+  1800

TAAACCTTTCTTTACACTCTGAGGTCTCCAAAACATTTGTTGTTATCAAAAAAAAAAAAA
1801  ---------+---------+---------+---------+---------+---------+  1860

AAAAAAAAAAAAAAAAAAAAAGCGGCCGC
1861  ---------+---------+---------  1889
```

Fig. 2B

```
                          SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
          (A) LENGTH: 1761 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:1:

CGCTCCCGCC GCAGTCGCCG GGCCATGGGC CTCGAGCCCG CCCCGAACCC CCGCGAGCCC      60

GCCTTGTCTG CGGCGTGACT GGAGGCCCAG ATGGTCATCA TGGGCCAGTG CTACTACAAC     120

GAGACCATCG GTTTCTTCTA TAACAACAGT GGCAAAGAGC TCAGCTCCCA CTGGCGGCCC     180

AAGGATGTGG TCGTGGTGGC ACTGGGGCTG ACCGTCAGCG TGCTGGTGCT GCTGACCAAT     240

CTGCTGGTCA TAGCAGCCAT CGCCTCCAAC CGCCGCTTCC ACCAGCCCAT CTACTACCTG     300

CTCGGCAATC TGGCCGCGGC TGACCTCTTC GCGGGCGTGG CCTACCTCTT CCTCATGTTC     360

CACACTGGTC CCCGCACAGC CCGACTTTCA CTTGAGGGCT GGTTCCTGCG GCAGGGCTTG     420

CTGGACACAA GCCTCACTGC GTCGGTGGCC ACACTGCTGG CCATCGCCGT GGAACGGCAC     480

CGCAGTGTGA TGGCCGTACA GTTGCACAGC CGCCTGCCCC GTGGCCGCGT GGTCATGCTC     540

ATTGTGGGCG TGTGGGTGGC TGCCCTGGGC CTGGGGCTGT TGCCTGCCCA CTCCTGGCAC     600

TGCCTCTGTG CCCTGGACCG CTGCTCACGC ATGGCACCCC TGCTCAGCCG CTCCTATTTG     660

GCCGTCTGGG CTCTGTCGAG CCTGCTTGTC TTCCTGCTCA TGGTGGCTGT GTACACCCGC     720

ATTTTTTTAT ACGTGCGGCG GCGAGTGCAG CGCATGGCAG AGCATGTCAG CTGCCACCCC     780

CGCTACCGAG AGACCACGCT CAGCCTGGTC AAGACTGTTG TCATCATCCT GGGGGCGTTC     840

GTGGTCTGCT GGACACCAGG CCAGGTGGTA CTGCTCCTGG ATGGTTTAGG CTGTGAGTCC     900

TGCAATGTCC TGGCTGTAGA AAAGTACTTC CTACTGTTGG CCGAGGCCAA CTCACTGGTC     960

AATGCTGCTG TGTACTCTTG CCGAGATGCT GAGATGCGCC GCACCTTCCG CCGCCTTCTC    1020

TGCTGCGCGT GCCTCCGCCA GCCCACCCGC GAGTCTGTCC ACTATACATC CTCTGCCCAG    1080

GGAGGTGCCA GCACTCGCAT CATGCTTCCC GAGAACGGCC ACCCACTGAT GGACTCCACC    1140

CTTTAGCTAC CTTGAACTTC AGCGGTACGC GGCAAGCAAC AAATCCACAG CCCCTGATGA    1200

CTTGTGGGTG CTCCTGGCTC AACCCAACCA ACAGGACTGA CTGACCGGCA GGACAAGGTC    1260

TGGCATGGCA CAGCACCACT GCCAGGCCTC CCCAGGCACA CCACTCTGCC CAGGGAATGG    1320

GGGCTTTGGG TCATCTCCCA CTGCCTGGGG GAGTCAGATG GGGTGCAGGA ATCTGGCTCT    1380

TCAGCCATCC CAGGTTTAGG GGGTTTGTAA CAGACATTAT TCTGTTTTCA CTGCGTATCC    1440

TTGGTAAGCC CTGTGGACTG GTTCCTGCTG TGTGATGCTG AGGGTTTTAA GGTGGGGAGA    1500

GATAAGGGCT CTCTCGGGCC ATGCTACCCG GTATGACTGG GTAATGAGGA CAGACTGTGG    1560

ACACCCCATY TACCTGAGTC TGATTCTTTA GCAGCAGAGA CTGAGGGGTG CAGAGTGTGA    1620
```

```
GCTGGGAAAG GTTTGTGGCT CCTTGCAGCC TCCAGGGACT GGCCTGTCCC CGATAGAATT        1680

GAAGCAGTCC ACGGGGAGGG GATGATACAA GGAGTAAACC TTTCTTTACA CTCTGAGGTC        1740

TCCAAAACAT TGTTGTTAT C                                                   1761
```

(2) INFORMATION FOR SEQ ID NO:2:

(i) SEQUENCE CHARACTERISTICS:
        (A) LENGTH: 351 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Leu Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255

Gly Gln Val Val Leu Leu Leu Asp Gly Leu Gly Cys Glu Ser Cys Asn
            260                 265                 270

Val Leu Ala Val Glu Lys Tyr Phe Leu Leu Leu Ala Glu Ala Asn Ser
        275                 280                 285

Leu Val Asn Ala Ala Val Tyr Ser Cys Arg Asp Ala Glu Met Arg Arg
    290                 295                 300

Thr Phe Arg Arg Leu Leu Cys Cys Ala Cys Leu Arg Gln Pro Thr Arg
305                 310                 315                 320

Glu Ser Val His Tyr Thr Ser Ser Ala Gln Gly Gly Ala Ser Thr Arg
```

```
               325                 330                 335
Ile Met Leu Pro Glu Asn Gly His Pro Leu Met Asp Ser Thr Leu
              340                 345                 350
```

(2) INFORMATION FOR SEQ ID NO:3:

(i) SEQUENCE CHARACTERISTICS:
        (A) LENGTH: 1889 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
TTACGAATTA ATACGATCAC TATAGGAGA CCAAGCTTGG TACCGAGCTC GGATCCACTA      60
GTAACGGCCG CCAGTGTGGG GAATTCCGCT CCCGCCGCAG TCGCCGGGCC ATGGGCCTCG    120
AGCCCGCCCC GAACCCCCGC GAGCCCGCCT TGTCTGCGGC GTGACTGGAG CCCAGATGG     180
TCATCATGGG CCAGTGCTAC TACAACGAGA CCATCGGTTT CTTCTATAAC AACAGTGGCA    240
AAGAGCTCAG CTCCCACTGG CGGCCCAAGG ATGTGGTCGT GGTGGCACTG GGGCTGACCG    300
TCAGCGTGCT GGTGCTGCTG ACCAATCTGC TGGTCATAGC AGCCATCGCC TCCAACCGCC    360
GCTTCCACCA GCCCATCTAC TACCTGCTCG GCAATCTGGC CGCGGCTGAC CTCTTCGCGG    420
GCGTGGCCTA CCTCTTCCTC ATGTTCCACA CTGGTCCCCG CACAGCCCGA CTTTCACTTG    480
AGGGCTGGTT CCTGCGGCAG GGCTTGCTGG ACACAAGCCT CACTGCGTCG GTGGCCACAC    540
TGCTGGCCAT CGCCGTGGAA CGGCACCGCA GTGTGATGGC CGTACAGTTG CACAGCCGCC    600
TGCCCCGTGG CCGCGTGGTC ATGCTCATTG TGGGCGTGTG GGTGGCTGCC CTGGGCCTGG    660
GGCTGTTGCC TGCCCACTCC TGGCACTGCC TCTGTGCCCT GGACCGCTGC TCACGCATGG    720
CACCCCTGCT CAGCCGCTCC TATTTGGCCG TCTGGGCTCT GTCGAGCCTG CTTGTCTTCC    780
TGCTCATGGT GGCTGTGTAC ACCCGCATTT TTTTATACGT GCGGCGGCGA GTGCAGCGCA    840
TGGCAGAGCA TGTCAGCTGC CACCCCCGCT ACCGAGAGAC CACGCTCAGC CTGGTCAAGA    900
CTGTTGTCAT CATCCTGGGG GCGTTCGTGG TCTGCTGGAC ACCAGGCCAG GTGGTACTGC    960
TCCTGGATGT TTTAGGCTGT GAGTCCTGCA ATGTCCTGGC TGTAGAAAAG TACTTCCTAC   1020
TGTTGGCCGA GGCCAACTCA CTGGTCAATG CTGCTGTGTA CTCTTGCCGA GATGCTGAGA   1080
TGCGCCGCAC CTTCCGCCGC CTTCTCTGCT GCGCGTGCCT CCGCCAGCCC ACCCGCGAGT   1140
CTGTCCACTA TACATCCTCT GCCCAGGGAG GTGCCAGCAC TCGCATCATG CTTCCCGAGA   1200
ACGGCCACCC ACTGATGGAC TCCACCCTTT AGCTACCTTG AACTTCAGCG GTACGCGGCA   1260
AGCAACAAAT CCACAGCCCC TGATGACTTG TGGGTGCTCC TGGCTCAACC CAACCAACAG   1320
GACTGACTGA CCGGCAGGAC AAGGTCTGGC ATGGCACAGC ACCACTGCCA GGCCTCCCCA   1380
GGCACACCAC TCTGCCCAGG GAATGGGGGC TTTGGGTCAT CTCCCACTGC CTGGGGGAGT   1440
CAGATGGGGT GCAGGAATCT GGCTCTTCAG CCATCCCAGG TTTAGGGGGT TTGTAACAGA   1500
CATTATTCTG TTTTCACTGC GTATCCTTGG TAAGCCCTGT GGACTGGTTC CTGCTGTGTG   1560
ATGCTGAGGG TTTTAAGGTG GGGAGAGATA AGGGCTCTCT CGGGCCATGC TACCCGGTAT   1620
GACTGGGTAA TGAGGACAGA CTGTGGACAC CCCATYTACC TGAGTCTGAT TCTTTAGCAG   1680
CAGAGACTGA GGGGTGCAGA GTGTGAGCTG GGAAAGGTTT GTGGCTCCTT GCAGCCTCCA   1740
GGGACTGGCC TGTCCCCGAT AGAATTGAAG CAGTCCACGG GGAGGGGATG ATACAAGGAG   1800
TAAACCTTTC TTTACACTCT GAGGTCTCCA AAACATTTGT TGTTATCAAA AAAAAAAAA    1860
```

-continued

```
AAAAAAAAAA AAAAAAAAAA AGCGGCCGC                              1889

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GGTGGTACTG CTCCTGGATG GTTTAG                                   26

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGGAGGCACG CGCAGCAGAG AAGA                                     24

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TAGAGAACCC ACTGCTTAC                                           19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCCAGAATAG AATGACACC                                           19
```

ISOLATED POLYNUCLEOTIDE FOR NOVEL G-PROTEIN COUPLED RECEPTOR

FIELD OF THE INVENTION

The present invention is in the field of molecular biology; more particularly, the present invention describes a nucleic acid sequence and an amino acid sequence for a novel human EDG-6 receptor homolog.

BACKGROUND OF THE INVENTION

The family of edg receptors are commonly grouped with orphan receptors because their endogenous ligands are not known (for example see Hla T and Maciag T (1990) J. Biol. Chem. 265:9308–13 ; U.S. Pat. No. 5,585,476). Recently, however, lysophospatidic acid has been demonstrated to be the endogenous ligand for the edg-2 receptor (Hecht et al. (1996) J. Cell. Biol. 135: 1071–1083; An et al. (1997) Biochem. Biophys. Res. Comm. 213: 619–622).

The edg family of receptors are seven transmembrane G protein coupled receptors (T7Gs). T7Gs are so named because of their seven hydrophobic domains which span the plasma membrane and form a bundle of antiparallel α helices. These transmembrane segments (TMS) are designated by roman numerals I–VII and account for structural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. The activated receptor, in turn, interacts with an intracellular G-protein complex which mediates further intracellular signaling activities generally the production of second messengers such as cyclic AMP (cAMP), phospholipase C, inositol triphosphate or ion channel proteins.

T7G receptors are expressed and activated during numerous developmental and disease processes. Identification of a novel T7G receptor provides the opportunity to diagnose or intervene in such processes, and the receptor can be used in screening assays to identify physiological or pharmaceutical molecules which trigger, prolong or inhibit its activity.

SUMMARY OF THE INVENTION

The invention provides a unique nucleotide sequence which encodes a novel human EDG-6 receptor homolog (HEDG). Herein, the nucleotide sequence encoding HEDG is designated hedg.

The invention relates to the use of nucleic acid and amino acid sequences of hedg, or its variants, in the diagnosis or treatment of diseased cells and/or tissues associated with aberrant expression of hedg. Aspects of the invention include the antisense DNA of hedg; cloning or expression vectors containing hedg; host cells or organisms transformed with expression vectors containing hedg; a method for the production and recovery of purified HEDG from host cells: purified protein, HEDG, which can be used to identify inhibitors for the downregulation of signal transduction involving HEDG; and methods of screening for ligands of hedg using transformed cells.

BRIEF DESCRIPTION OF THE DRAWINGS

FIGS. 1A through 1E show the alignment of the nucleic acid sequence (coding region of SEQ. ID NO: 1) and amino acid sequence (SEQ. ID NO:2) for HEDG.

FIGS. 2A and 2B display the nucleic acid sequence (SEQ. ID NO:3) of a cDNA encoding HEDG.

DETAILED DESCRIPTION OF THE INVENTION

As used herein and designated by the upper case abbreviation, HEDG, refers to an EDG-6 receptor homolog in either naturally occurring or synthetic form and active fragments thereof which have the amino acid sequence of SEQ. ID NO:2. In one embodiment, the polypeptide HEDG is encoded by mRNAs transcribed from the cDNA, as designated by the lower case abbreviation, hedg, of SEQ. ID NO: 1.

The novel human EDG-6 receptor homolog, HEDG, was cloned and isolated from a human kidney proximal tubule cDNA library. It shows 52.9% identity to human edg-2 (WO 97/00952).

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or be chemically synthesized. They are useful in detecting the presence of identical or similar sequences.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After protesting to optimize reaction conditions and to eliminate false positives, nucleic acid probes may be used in southern, northern or in situ hybridizations to determine whether DNA or RNA encoding HEDG is present in a cell type, tissue, or organ.

"Reporter" molecules are those radionuclides, enzymes, fluorescent, chemiluminescent, or chromogenic agents which associate with, establish the presence of, and may allow quantification of a particular nucleotide or amino acid sequence.

"Recombinant nucleotide variants" encoding HEDG may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system, respectively.

"Chimeric" molecules may be constructed by introducing all or part of the nucleotide sequence of this invention into a vector containing additional nucleic acid sequence which might be expected to change any one (or more than one) of the following HEDG characteristics: cellular location, distribution, ligand-binding affinities, interchain affinities, degradation/turnover rate, signaling, etc.

"Active" refers to those forms, fragments, or domains of any HEDG polypeptide which retain the biological and/or antigenic activities of any naturally occurring HEDG.

"Naturally occurring HEDG" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to those polypeptides which have been chemically modified by such techniques as ubiquitination, labeling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring HEDG by amino acid insertions, deletions and/or substitutions, created using recombinant DNA techniques. Guidance in determining which amino acid residues may be replaced, added or deleted without abolishing activities of interest may be found by comparing the sequence of HEDG with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically or by systematically making insertions, deletions, or substitutions of nucleotides in the hedg sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard" expression is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (cats dogs, etc.), agricultural (cows, horses, sheep, etc.) or test species (mouse, rat, rabbit, etc.).

The present invention provides a nucleotide sequence uniquely identifying a novel seven transmembrane receptor (T7G), human EDG-6 or HEDG. Based on the homology of HEDG to edg-2 it is likely that HEDG binds a ligand of the same chemical class. Edg-2 specifically binds lysophosphatidic acid (LPA) which is a phospholipid. Phospholipids have been demonstrated to be important regulators cell activity, including mitogenisis (Xu et al. (1995) J. Cell. Physiol., 163: 441–450) and apoptosis, cell adhesion and regulation of gene expression. Specifically, for example, LPA elicits growth factor-like effects on cell prolyeration (Moolenar (1996) J. Biol. Chem, 270: 12949–12952) and cell migration (Imamura et al. (1993) Biochem. Biophys. Res. Comm., 193: 497–503). It has also been suggested that LPA plays a role in wound healing and regeneration (Tigyi et al. (1992) J. Biol. Chem., 267: 21360–21367). Further, considerable circumstantial evidence indicates that phospholipids may be involved in various disease states including cancer (Imamura et al., (1993) Biochem. Biophys. Res. Comm., 193: 497–503); diseases having an inflammatory component (Fourcade et al. (1995), Cell, 80(6): 919–927, including adult respiratory distress, neurodegeneration (Jalink et al. (1993) Cell Growth Differ., 4: 247–255), rheumatoid arthritis (Natiarajan et al. (1995) J. Lipid Res., 36(9): 2005–2016), psoriasis and inflammatory bowel disease. Thus, the ligand for HEDG is likely to be a biologically important regulator of cell activity, and therefore aberrant expression of HEDG is likely to be associated with a chronic or acute disease states. Further, modulators of HEDG activity are likely to be useful in treatment or prevention of such disease states.

HEDG ligands are likely to be found among the phospholipid class of compounds. Therefore, preferably phospholipid molecules should be screened to identify HEDG ligands. More preferably, lysophospholipds should be screened. Even more preferably, lysoglycerophospholipids should be screened. Most preferably, LPA, lysophosphatidylethanolamine (LPE), lysophosphatidylserine (LPS), lysophosphatidylinositol (LPI), lysophosphatidylcholine (LPC), lyso-platelet activating factor (lyso-PAF) and phosphatidic acid should be screened.

A diagnostic test for excessive expression of HEDG can accelerate diagnosis and proper treatment of abnormal conditions caused by viral, bacterial or fungal infections; allergic responses; mechanical injury associated with trauma; hereditary diseases; lymphoma, leukemia or carcinoma: or other conditions which activate the genes of lymphoid or neuronal tissues.

The nucleotide sequences encoding HEDG (or their complement) have numerous applications in techniques known to those skilled in the art of molecular biology. These techniques include use as hybridization probes, use in the construction of oligomers for PCR, use for chromosome and gene mapping, use in the recombinant production of HEDG, and use in generation of antisense DNA or RNA, their chemical analogs and the like. Uses of nucleotides encoding HEDG disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of HEDG-encoding nucleotide sequences may be produced. Some of these will only bear minimal homology to the nucleotide sequence of the known and naturally occurring HEDG. The invention has specifically contemplated each and every possible variation of nucleotide sequence that could be made by selecting combinations based on possible codon choices. These combinations are made in accordance with the standard triplet genetic code as applied to the nucleotide sequence of naturally occurring hedg, and all such variations are to be considered as being specifically disclosed.

Although the nucleotide sequences which encode HEDG, its derivatives or its variants are preferably capable of hybridizing to the nucleotide sequence of the naturally occurring hedg under stringent conditions, it may be advantageous to produce nucleotide sequences encoding HEDG or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding HEDG and/or its derivatives without altering the encoded aa sequence include the production of RNA transcripts having more desirable properties, such as a greater half-life, than transcripts produced from the naturally occurring sequence.

Nucleotide sequences encoding HEDG may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City). Useful nucleotide sequences for joining to hedg include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for hedg-specific hybridization probes capable of hybridizing with naturally occurring nucleotide sequences encoding HEDG. Such probes may also be used for the detection of similar T7G encoding sequences and should preferably contain at least 40% nucleotide identity to hedg sequence. The hybridization probes of the subject invention may be derived from the nucleotide sequence presented as SEQ. ID NO: 1 or from genomic sequences including promoter, enhancers or introns of the native gene. Hybridization probes may be labeled by a variety of reporter molecules using techniques well known in the art.

It will be recognized that many deletional or mutational analogs of nucleic acid sequences for HEDG will be effective hybridization probes for HEDG nucleic acid. Accordingly, the invention relates to nucleic acid sequences that hybridize with such HEDG encoding nucleic acid sequences under stringent conditions.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Such hybridization conditions are described by Sambrook et al., Molecular Cloning: A Laboratory Manual, 2nd ed., Cold Spring Harbor Press, 1989. Hybridization conditions and probes can be adjusted in well-characterized ways to achieve selective hybridization of human-derived probes.

Nucleic acid molecules that will hybridize to HEDG encoding nucleic acid under stringent conditions can be identified functionally, using methods outlined above, or by using for example the hybridization rules reviewed in Sambrook et al., Molecular Cloning: A Laboratory Manual, 2nd ed., Cold Spring Harbor Press, 1989.

Without limitation, examples of the uses for hybridization probes include: histochemical uses such as identifying tissues that express HEDG; measuring mRNA levels, for instance to identify a sample's tissue type or to identify cells that express abnormal levels of HEDG; and detecting polymorphisms in the HEDG. RNA hybridization procedures are described in Maniatis et al. Molecular Cloning, a Laboratory Manual (Cold Spring Harbor Press, 1989).

PCR as described U.S. Pat. Nos. 4,683,195; 4,800,195; and 4,965,188 provides additional uses for oligonucleotides based upon the nucleotide sequence which encodes HEDG. Such probes used in PCR may be of recombinant origin, chemically synthesized, or a mixture of both. Oligomers may comprise discrete nucleotide sequences employed under optimized conditions for identification of hedg in specific tissues or diagnostic use. The same two oligomers, a nested set of oligomers, or even a degenerate pool of oligomers may be employed under less stringent conditions for identification of closely related DNA's or RNA's.

Rules for designing polymerase chain reaction ("PCR") primers are now established, as reviewed by PCR Protocols, Cold Spring Harbor Press, 1991. Degenerate primers, i.e., preparations of primers that are heterogeneous at given sequence locations, can be designed to amplify nucleic acid sequences that are highly homologous to, but not identical to hedg. Strategies are now available that allow for only one of the primers to be required to specifically hybridize with a known sequence. See, Froman et al., Proc. Natl. Acad. Sci. U.S.A. 85: 8998, 1988 and Loh et al., Science 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, PCR Protocols, Cold Spring Harbor Press, 1991.

Other means of producing specific hybridization probes for hedg include the cloning of nucleic acid sequences encoding HEDG or HEDG derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

The nucleotide sequence for hedg can be used in an assay to detect inflammation or disease associated with abnormal levels of HEDG expression. The cDNA can be labeled by methods known in the art, added to a fluid, cell or tissue sample from a patient, and incubated under hybridizing conditions. After an incubation period, the sample is washed with a compatible fluid which optionally contains a reporter molecule. After the compatible fluid is rinsed off, the reporter molecule is quantitated and compared with a standard as previously defined.

The nucleotide sequence for hedg can be used to construct hybridization probes for mapping the native gene. The gene may be mapped to a particular chromosome or to a specific region of a chromosome using well known mapping techniques. These techniques include in situ hybridization of chromosomal spreads (Verma et al (1988) Human Chromosomes: A Manual of Basic Techniques, Pergamon Press, New York City), flow-sorted chromosomal preparations, or artificial chromosome constructions such as yeast artificial chromosomes (YACs), bacterial artificial chromosomes (BACs), bacterial P1 constructions or single chromosome cDNA libraries.

In situ hybridization of chromosomal preparations and physical mapping techniques such as linkage analysis using established chromosomal markers are invaluable in extending genetic maps. Examples of genetic map data can be found in the yearly genome issue of Science (e.g. 1994, 265:1981f). Often locating a gene on the chromosome of another mammalian species may reveal associated markers which can be used to help identify the analagous human chromosome.

New nucleotide sequences can be assigned to chromosomal subregions by physical mapping. The mapping of new genes or nucleotide sequences provide useful landmarks for investigators searching for disease genes using positional cloning or other gene discovery techniques. Once a disease or syndrome, such as ataxia telangiectasia (AT), has been crudely localized by genetic linkage to a particular genomic region, for example, AT to 1 1q22-23 (Gatti et al (1988) Nature 336:577–580), any sequences mapping to that area may represent or reveal genes for further investigation. The nucleotide sequence of the subject invention may also be used to detect differences in gene sequence between normal and carrier or affected individuals.

Nucleotide sequences encoding hedg may be used to produce a purified oligo—or polypeptide using well known methods of recombinant DNA technology. Goeddel (1990, Gene Expression Technology, Methods and Enzymology, Vol. 185, Academic Press, San Diego Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding HEDG may be cultured under conditions suitable for the expression of T7Gs, their extracellular, transmembrane or intracellular domains and recovery of such peptides from cell culture. HEDG (or any of its domains) produced by a recombinant cell may be secreted or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from hedg or a desired portion of the polypeptide to a nucleic acid sequence encoding a polypeptide domain which will facilitate protein purification (Kroll DJ et al (1993) DNA Cell Biol. 12:441–53).

In addition to recombinant production, fragments of HEDG may be produced by direct peptide synthesis using solid-phase techniques (e.g. Stewart at al (1969) Solid-Phase Peptide Synthesis, WH Freeman Co., San Francisco Calif.; Merrifield J (1963) J Am Chem. Soc. 85:2149–2154). Automated synthesis may be achieved, for example, using Applied Biosystems 431A Peptide Synthesizer (Foster City, Calif.) in accordance with the instructions provided by the manufacturer. Additionally, a particular portion of HEDG may be mutated during direct synthesis and combined with other parts of the peptide using chemical methods.

HEDG for antibody induction does not require biological activity: however, the protein must be antigenic. Peptides used to induce specific antibodies may have an aa sequence consisting of at least five amino acids (aa), preferably at least 10 aa. They should mimic a portion of the aa sequence of the protein and may contain the entire aa sequence of a small naturally occurring molecule such as HEDG. An antigenic portion of HEDG may be fused to another protein such as keyhole limpet hemocyanin, and the chimeric molecule used for antibody production.

Antibodies specific for HEDG may be produced by inoculation of an appropriate animal with the polypeptide or an antigenic fragment. An antibody is specific for HEDG if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (e.g. Orlandi R et al (1989) PNAS 86:3833–3837, or Huse W D et al (1989) Science 256:1275–1281) or the in vitro stimulation of lymphocyte populations. Current technology (Winter G and Mistein C (1991) Nature 349:293–299) provides for a number of highly specific binding reagents based on the principles of antibody formation. These techniques may be adapted to produce molecules which specifically bind HEDGs.

An additional embodiment of the subject invention is the use of HEDG specific antibodies, inhibitors, receptors or their analogs as bioactive agents to treat inflammation or disease including, but not limited to viral, bacterial or fungal infections; allergic responses; mechanical injury associated with trauma; hereditary diseases; lymphoma or carcinoma; or other conditions which activate the genes of lymphoid or neuronal tissues.

Bioactive compositions comprising agonists, antagonists, receptors or inhibitors of HEDG may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving excessive lymphocyte and leukocyte trafficking.

Rheumatoid arthritis is currently evaluated on the basis of swelling, response to NSAIDs, x-rays, etc. HEDG is most likely expressed on the surface of the fibroblasts, T and B lymphocytes, monocytelmacrophages, or mast cells which comprise the cells of the inflamed synovium. Once adequate standards are established, an assay for the abnormal expression of HEDG is a viable diagnostic tool for assessing the extent that RA has progressed. The expression of HEDG in a sustained inflammatory response makes it a valuable therapeutic target for screening drug libraries. Inhibitors of HEDG are useful for controlling signal transduction and signaling cascades in cells of the rheumatoid synovium.

The examples below are provided to illustrate the subject invention. These examples are provided by way of illustration and are not included for the purpose of limiting the invention.

EXAMPLES

Isolation of Human edg-6 cDNA

Example 1

PCR Amplification of edg-6 cDNA from a Human Kidney Proximal Tubule cDNA Library PCR reactions were conducted using EDG6-F1 or EDG6-R1 primers vs primers derived from the pcDNA3 expression vector (Invitrogen catalog no. V790-20) in which this human kidney proximol tubule cDNA library was constructed (ATCC 87306).

```
                                              SEQ ID NO: 4
EDG6-F1 5'-GGTGGTACTGCTCCTGGATGGTTTAG-3'
                                              SEQ ID NO: 5
EDG6-R1 5'-CGGAGGCACGCGCAGCAGAGAAGA-3'
```

830F: [5'-TAGAGAACCCACTGCTTAC-3'] SEQ ID NO:6
1186R: [5'-CCCAGAATAGAATGACACC-3'] SEQ ID NO:7

One PCR reaction was done with EDG6-F1 vs 1186R primers (representing the 3' end of edg-6 cDNA clones), and another was done with 830F vs EDG6-R1 primers (representing the 5' end of edg-6 cDNA clones). Each 40 µl reaction contained the following reagents:

| 26.4 µl | water |
|---|---|
| 5.6 µl | 2.5 mM dNTP mix |
| 4 µl | 10x Expand ™ Buffer 1 (Boehringer Mannheim Cat. No. 1681-842) |
| 1.2 µl | 10 µM EDG6-specific primer |
| 1.2 µl | 10 µM vector primer |
| 0.6 µl | Expand PCR enzyme (0.4 units) |
| 1 µl | diluted ATCC 87306 cDNA library stock (≧1 library equivalent/µl) |

PCR Conditions:

| Incubate: | 94° C. for 2 min |
|---|---|
| 30 cycles: | 92° C. for 30 sec |
| | 55° C. for 30 sec |
| | 68° C. for 3 min |
| Incubate: | 68° C. for 8 min |
| Hold: | 4° C. |

The results showed 2 bands from the 3'-end cDNA reaction (EDG6-F1/1186R). The predominant band was 1.0 kb in length (designated 3'-2), while a fainter 1.6 kb band was also seen (3'-1). From the 5'-end reaction (830F/EDG6-R1) at least 8 bands were seen, ranging from about 1.7 kb to less than 500 bp. These bands were designated 5'-1, 5'-2, 5'-3, 5'-4, 5'-5, 5'-6, 5'-7 and 5'-8, in order from largest to smallest sized PCR products.

Each band was tip-eluted from the gel by stabbing the band with a fresh yellow Pipetman tip, which was then rinsed into 50 µl of TE, pH 8. Both 3'-1 and 3'-2 were picked separately, along with the eight 5' bands. The 50 µl solutions were then used as a stock from which reamplifications were done using the same primers as in the original reaction, as follows:

| 12.7 µl | water |
|---|---|
| 2.8 µl | 2.5 mM dNTP mix |
| 2 µl | 10x Expand ™ Buffer 1 |
| 0.6 µl | 10 µM EDG6-specific primer |
| 0.6 µl | 10 µM vector primer |
| 0.3 µl | Expand PCR enzyme (0.4 units) |
| 1 µl | tip-eluted DNA stock |

PCR Conditions:

| Incubate: | 94° C. for 2 min |
|---|---|
| 30 cycles: | 92° C. for 30 sec |
| | 55° C. for 30 sec |
| | 68° C. for 3 min |
| Incubate: | 68° C. for 8 min |
| Hold: | 4° C. |

Sequencing was carried out using Applied Biosystems Inc. sequencing kit (catalog no. 402078). Sequencing of the reamplified products determined that only three of the eight 5' PCR products (5'-4, 5'-5 and 5'-8) and one of the two 3' PCR products (3'-2) matched the edg-6 cDNA. This analysis also suggested that the longest 5' PCR product, 5'-4, contained the translation initiation codon and complete 5' portion of edg-6 coding sequence. In addition, the one 3' PCR product, 3'-2, contained the complete 3' portion of edg-6 coding sequence, including an extended 3'-untranslated region and 34 bp poly(A) tail, characteristic of eukaryotic mRNAs.

Full-length Cloning of the Human edg-6 cDNA into pcDNA3 Vector

Extension PCR (cycles without primers) was used to join the overlapping ~1.2 kb 5'-4 fragment and 1.0 kb 3'-2 fragment as follows:

Extension PCR:

| 12.2 µl | water |
|---|---|
| 2.8 µl | 2.5 mM dNTP mix |
| 2 µl | 10x Expand ™ Buffer 1 |
| 1 µl | edg-6 5'-4 PCR product |
| 1 µl | edg-6 3'-2 PCR product |
| 1 µl | Expand PCR enzyme (3.5 units) |

PCR Conditions:

| Incubate: | 94° C. for 2 min |
|---|---|
| 10 cycles: | 92° C. for 1 min |
| | 65° C. for 2 min |
| | 68° C. for 3 min |
| Incubate: | 68° C. for 5 min |
| Hold: | 4° C. |

The following mix was then added:

| 56.3 µl | water |
|---|---|
| 11.2 µl | 2.5 mM dNTP mix |
| 8 µl | 10x Expand ™ Buffer 1 |
| 1.5 µl | 10 µM 830F primer |
| 1.5 µl | 10 µM 1186R primer |
| 1.5 µl | Expand PCR enzyme (3.5 units/µl) |

PCR Conditions:

| Incubate: | 94° C. for 2 min |
|---|---|
| 30 cycles: | 92° C. for 30 sec |
| | 65° C. for 30 sec |
| | 68° C. for 3 min |
| Incubate: | 68° C. for 8 min |
| Hold: | 4° C. |

After gel electrophoresis of the PCR products, a weak DNA band of about 2.2 kb was seen. Reamplification was performed at a lower annealing temperature using 5 ul of this PCR material in the following PCR reaction:

Reamplification PCR:

| 63.5 µl | water |
|---|---|
| 14 µl | 2.5 mM dNTP mix |
| 10 µl | 10x Expand ™ Buffer 1 |
| 3 µl | 10 µM 830F primer |
| 3 µl | 10 µM 1186R primer |
| 1.5 µl | Expand PCR enzyme (3.5.units/µl) |
| 5 µl | DNA from previous PCR reaction |

PCR Conditions:

| Incubate: | 94° C. for 2 min |
|---|---|
| 30 cycles: | 92° C. for 30 sec |
| | 50° C. for 30 sec |
| | 68° C. for 3 min |
| Incubate: | 68° C. for 8 min |
| Hold: | 4° C. |

On gel electrophoresis, an intense PCR product was seen at 2.2 kb. This product was gel purified from 20 µl of the PCR reaction, by cutting the appropriate band from the gel and recovering the DNA with a Qiaquick gel extraction kit from Qiagen Inc. (Cat no. 28706) in 25 ul of 10 mM Tris (pH 8.5).

Restriction digest of PCR sample with KpnI and XhoI:

A double digest was performed on 5 µl of the purified reamplified PCR reaction as follows:

| 5 µl | Reamplified, gel-purified PCR DNA |
|---|---|
| 5 µl | 10X NEBuffer 2 (New England Biolabs [NEB]) |
| 1 µl | KpnI restriction endonuclease (10 units; NEB, Cat #142S) |
| 1 µl | XhoI restriction endonuclease (20 units; NEB, Cat #146S) |
| 5 µl | 10X Acetylated BSA stock (NEB) |
| 33 µl | water |

The restriction digest was incubated for 1 hour in a 37° C. water block heater. The reaction products were run on a gel, the ~2 kb DNA band was cut out and purified from the gel in 10 µl of 10 mM Tris (pH 8.5).

Preparation of pcDNA3 cloning vector with KpnI and XhoI:

| 4 µl | pcDNA3 plasmid DNA containing a 1.8 kb cDNA insert |
|---|---|
| 10 µl | 10X NEBuffer 2 (NEB) |
| 3 µl | KpnI restriction endonuclease (NEB: 1:10 dilution; 3 units) |
| 3 µl | XhoI restriction endonuclease (NEB: 1:20 dilution; 3 units) |
| 10 µl | 10X Acetylated BSA stock (NEB) |
| 64 µl | water |

The vector DNA was digested for 1 hour at 37° C. Then, 3 units more of each enzyme was added and the tubes were incubated for a further 2 hr at 37° C. The digest was run on a gel, and the vector band without cDNA insert was cut out and purified using GeneCleanII kit (BIO 101) and eluted in 40 µl of 10 mM Tris (pH 8.5).

The double-digested, gel-purified PCR DNA was ligated into the prepared pcDNA3 plasmid vector using T4 DNA ligase kit (NEB, Cat #202CS) and transformed into Epicurean Coli XL-2 Blue MRF' Ultracompetent cells (Stratagene, Cat #200150). The transformation was plated onto 2×YT/Ampicillin plates and single colonies were picked. DNA minipreps were made using QIAGEN QIAPrep 8 miniprep kit (Cat #27144) and clones with appropriate inserts were identified by sequencing, carried out with the in-house ABI automated sequencing system. From this analysis, a full length clone designated pC3-hEdg6 was chosen for complete sequence determination of the cDNA insert.

An open reading frame of 1053 bp constitutes the coding region of human edg-6. This coding region starts with a methionine codon at nt 91 (FIG. 1, SEQ ID NO:1), preceded by an in-frame translation initiation codon (TGA) at nt 76–78. Translation is terminated by a stop codon at nt 1144.

The edg-6 open reading frame of the pC3-hEdg6 clone predicts a 351 amino acid polypeptide with many typical features of a G protein-coupled receptor (GPCR). These include:

1. A hydropathy profile consistent with the 7 transmembrane structure of GPCRs:

N-terminal extracellular domain: 1–33

Transmembrane region 1 (TM-1): 33–58

Intracellular loop-1 (IL-1) :59–65

TM-2: 66–94

Extracellular loop-1 (EL-1): 95–108

TM-3: 109–127

IL-2:128–146

TM-4: 147–172

EL-2: 173–188

TM-5: 189–209

IL-3: 210–241

TM-6: 242–263

EL-3: 264–278

TM-7: 279–299

2. C-terminal cytoplasmic domain: 300–351

Potential N-glycosylation sites in the extracellular N-terminal domain, residues 10 and 18

3. Potential N-myristoylation site at residue 331

Potential protein kinase C phosphorylation sites at residues 59, 305 and 334

The amino acid sequence of human edg-6 (FIG. 1, SEQ ID NO:2) also shows very good conservation with other members of the edg subfamily of GPCRs. The pairwise percent identity is presented in the Table 1 below:

TABLE 1

Percent identity and percent similarity at the amino acid level of edg family to the human edg-6 receptor

| Gene | Percent Identity | Percent Similarity |
|---|---|---|
| Edg-1 (Human) | 33.7 | 56.0 |
| Edg-2 (Human) | 52.9 | 71.7 |
| Edg-3 (Human) | 33.9 | 56.5 |
| H218 (Edg-4: Rat) | 35.9 | 56.6 |

Example 2

Homology Searching of cDNA Clones and Deduced Proteins

A FASTA search (GCG, FASTA version 3.0) against daily-updated in-house databases comprised of Genbank, EMBL, dbEST, the HTG, GSS and STS genomic sequencing databases revealed several sequence related to human edg-6. First, in addition to the original EST (T02954) found by database mining, 1 additional EST (Genbank W60555) closely matched the edg-6 sequence (98.4% identity in a 386 nt overlap from nt 1078–1463). Second, the murine LPA receptor, edg-2, was the highest-scoring full-length cDNA sequence found from the combined Genbank/EMBL databases (Genbank MMU70622: 62.8% identity in 980 nt overlap from nt 106–1073). A lower degree of sequence identity was seen with the edg-1 orphan receptor (Genbank HUMEDG: 55.0% identity in 767 nt overlap from nt 277–1026).

Example 3

Antisense Analysis

Knowledge of the correct, complete cDNA sequence of HEDG enables its use as a tool for antisense technology in the investigation of gene function. Oligonucleotides, cDNA or genomic fragments comprising the antisense strand of hedg are used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to trans-acting regulatory genes. Similarly, inhibition is achieved using Hogeboom base-pairing methodology, also known as "triple helix" base pairing.

Example 4

Expression of HEDG

Expression of hedg is accomplished by subcloning the cDNAs into appropriate expression vectors and transfecting the vectors into analogous expression hosts for example *E. coli*. In a particular case, the vector is engineered such that it contains a promoter for β-galactosidase, upstream of the cloning site, followed by sequence containing the amino-terminal Met and the subsequent 7 residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with IPTG using standard methods produces a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The hedg cDNA is shuttled into other vectors known to be useful for expression of protein in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells., insect cells such as Sf9 cells, yeast cells such as *Saccharomyces cerevisiae* and bacteria such as *E. coli*. For each of these cell systems, a useful expression vector also includes an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced HEDG are recovered from the conditioned medium and analyzed using chromatographic methods known in the art. For example, HEDG can be expressibly cloned into the expression vector pcDNA3, as exemplified herein. This product can be used to transform, for example, HEK293 or COS by methodology standard in the art. Specifically, for example, using Lipofectamine (Gibco BRL catolog no. 18324-020) mediated gene transfer.

Example 5

Isolation of Recombinant HEDG

HEDG is expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of a cleavable linker sequence such as Factor XA or enterokinase (Invitrogen) between the purification domain and the HEDG sequence is useful to facilitate expression of HEDG.

Example 6

Testing of Chimeric T7Gs

Functional chimeric T7Gs are constructed by combining the extracellular receptive sequences of a new isoform with the transmembrane and intracellular segments of a known isoform for test purposes. This concept was demonstrated by Kobilka et al (1988, Science 240:1310–1316) who created a series of chimeric α2-β2 adrenergic receptors (AR) by inserting progressively greater amounts of α2-AR transmembrane sequence into β2-AR. The binding activity of known agonists changed as the molecule shifted from having more α2 than β2 conformation, and intermediate constructs demonstrated mixed specificity. The specificity for binding antagonists, however, correlated with the source of the domain VII. The importance of T7G domain VII for ligand recognition was also found in chimeras utilizing two yeast α-factor receptors and is significant because the yeast receptors are classified as miscellaneous receptors. Thus, functional role of specific domains appears to be preserved throughout the T7G family regardless of category.

In parallel fashion, internal segments or cytoplasmic domains from a particular isoform are exchanged with the analogous domains of a known T7G and used to identify the structural determinants responsible for coupling the receptors to trimeric G-proteins (Dohlman et al (1991) Annu Rev Biochem 60:653–88). A chimeric receptor in which domains V, VI, and the intracellular connecting loop from β2-AR were substituted into a2-AR was shown to bind ligands with a2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V–>VI loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V–>VI loop is the major determinant for specificity of G-protein activity (Bolander FF, supra).

Chimeric or modified T7Gs containing substitutions in the extracellular and transmembrane regions have shown that these portions of the receptor determine ligand binding specificity. For example, two Ser residues conserved in domain V of all adrenergic and D catecholainine T7G receptors are necessary for potent agonist activity. These serines are believed to form hydrogen bonds with the catechol moiety of the agonists within the T7G binding site. Similarly, an Asp residue present in domain III of all T7Gs which bind biogenic amines is believed to form an ion pair with the ligand amine group in the T7G binding site.

Functional, cloned T7Gs are expressed in heterologous expression systems and their biological activity assessed (e.g. Marullo et al (1988) Proc Natl Acad Sci 85:7551–55; King et al (1990) Science 250:121–23) One heterologous system introduces genes for a mammalian T7G and a mammalian G-protein into yeast cells. The T7G is shown to have appropriate ligand specificity and affinity and trigger appropriate biological activation—growth arrest and morphological changes—of the yeast cells.

An alternate procedure for testing chimeric receptors is based on the procedure utilizing the $P_{2u}$ purinergic receptor ($P_{2u}$) as published by Erb et al (1993, Proc Natl Acad Sci 90:104411–53). Function is easily tested in cultured K562 human leukemia cells because these cells lack $P^{2u}$ receptors. K562 cells are transfected with expression vectors containing either normal or chimeric $P_{2u}$ and loaded with fura-a, fluorescent probe for $Ca^{++}$. Activation of properly assembled and functional $P_{2u}$ receptors with extracellular UTP or ATP mobilizes intracellular $Ca^{++}$ which reacts with fura-a and is measured spectrofluorometrically.

As with the T7G receptors above, chimeric genes are created by combining sequences for extracellular receptive segments of any newly discovered T7G polypeptide with the nucleotides for the transmembrane and intracellular segments of the known $P_{2u}$ molecule. Bathing the transfected K562 cells in microwells containing appropriate ligands triggers binding and fluorescent activity defining effectors of the T7G molecule. Once ligand and function are established, the $P_{2u}$ system is useful for defining antagonists or inhibitors which block binding and prevent such fluorescent reactions.

Example 7

Production of HEDG Specific Antibodies

Two approaches are utilized to raise antibodies to HEDG, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 micrograms are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate HEDG domain, as deduced from translation of the cDNA, is analyzed to determine regions of high antigenicity. Oligopeptides comprising appropriate hydrophilic regions, as illustrated in FIG. 1, SEQ ID NO:2, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis Mo.) by reaction with M-maleimidobenzoyl-N-hydroxysuccinimide ester (MBS; Ausubel FM et al, supra). If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine sewn albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled HEDG to identify those fusions producing the monoclonal antibody with the desired specificity. In a typical protocol, wells of plates (FAST; Becton-Dickinson, Palo Alto Calif.) are coated during incubation with affinity purified, specific rabbit anti-mouse (or suitable antispecies 1 g) antibodies at 10 mg/ml. The coated wells are blocked with 1% BSA, washed and incubated with supematants from hybridomas. After washing the wells are incubated with labeled HEDG at 1 mg/ml. Supernatants with specific antibodies bind more labeled HEDG than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascetic fluid by affinity chromatography on Protein A. Monoclonal antibodies with affinities of at least $10^8$ M$^{-1}$, preferably $10^9$ to $10^{10}$ or stronger, are typically made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

Example 8

Diagnostic Test Using HEDG Specific Antibodies

Particular HEDG antibodies are useful for investigating signal transduction and the diagnosis of infectious or hereditary conditions which are characterized by differences in the amount or distribution of HEDG or downstream products of an active signaling cascade.

Diagnostic tests for HEDG include methods utilizing antibody and a label to detect HEDG in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, Incorporated herein by reference.

A variety of protocols for measuring soluble or membrane-bound HEDG, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on HEDG is preferred, but a competitive binding assay may be employed. These assays are described, among other places, in Maddox, D E et al (1983, J Exp. Med. 158:1211f).

Example 9

Purification of Native HEDG Using Specific Antibodies

Native or recombinant HEDG is purified by immunoaffinity chromatography using antibodies specific for HEDG. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of HEDG by preparing a fraction from cells containing HEDG in a soluble form. This preparation is derived by solubilization of whole cells or of a subcellular fraction obtained via differential centrifugation (with or without addition of detergent) or by other methods well known in the art. Alternatively, soluble HEDG containing a signal sequence is secreted in useful quantity into the medium in which the cells are grown.

A soluble HEDG-containing preparation is passed over the immunoaffinity column, and the column is washed under conditions that allow the preferential absorbance of HEDG (e.g., high ionic strength buffers in the presence of detergent). Then, the column is eluted under conditions that disrupt antibody/protein binding (e.g., a buffer of pH 2–3 or a high concentration of a chaotrope such as urea or thiocyanate ion), and HEDG is collected.

Example 10

Drug Screening

This invention is particularly useful for screening therapeutic compounds by using HEDG or binding fragments thereof in any of a variety of drug screening techniques. As HEDG is a G protein couples receptor any of the methods commonly used in the art may potentially used to identify HEDG ligands. For example, the activity of a G protein coupled receptor such as HEDG can be measured using any of a variety of appropriate functional assays in which activation of the receptor results in an observable change in the level of some second messenger system, such as adenylate cyclase, guanylylcyclase, calcium mobilization, or inositol phospholipid hydrolysis. Alternatively, the polypeptide or fragment employed in such a test is either free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, are used for standard binding assays.

One measures, for example, the formation of complexes between HEDG and the agent being tested. Alternatively, one examines the diminution in complex formation between HEDG and a ligand caused by the agent being tested.

Thus, the present invention provides methods of screening for drugs or any other agents which affect signal transduction. These methods, well known in the art, comprise contacting such an agent with HEDG polypeptide or a fragment thereof and assaying (i) for the presence of a complex between the agent and the HEDG polypeptide or fragment, or (ii) for the presence of a complex between the HEDG polypeptide or fragment and the cell. In such competitive binding assays, the HEDG polypeptide or fragment is typically labeled. After suitable incubation, free HEDG polypeptide or fragment is separated from that present in bound form, and the amount of free or uncomplexed label is a measure of the ability of the particular agent to bind to HEDG or to interfere with the HEDG and agent complex.

Another technique for drug screening provides high throughput screening for compounds having suitable binding affinity to the HEDG polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with HEDG polypeptide and washed. Bound HEDG polypeptide is then detected by methods well known in the art. Purified HEDG are also coated directly onto plates for use in the aforementioned drug screening techniques. In addition, non-neutralizing antibodies are used to capture the peptide and immobilize it on the solid support.

This invention also contemplates the use of competitive drug screening assays in which neutralizing antibodies capable of binding HEDG specifically compete with a test compound for binding to HEDG polypeptides or fragments thereof. In this manner, the antibodies are used to detect the presence of any peptide which shares one or more antigenic determinants with HEDG.

Example 11

Rational Drug Design

The goal of rational drug design is to produce structural analogs of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo (e.g., Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design includes molecules which have improved activity or stability as shown by Braxton S and Wells J A (1992, Biochemistry 31:7796–7801) or which act as inhibitors, agonists, or antagonists of native peptides as shown by Athauda S B et al (1993 J Biochem 113:742–46), incorporated herein by reference.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the HEDG amino acid sequence provided herein provides guidance to those employing computer modeling techniques in place of or in addition to x-ray crystallography.

Example 12

Identification of Other Members of the Signal Transduction Complex

The inventive purified HEDG is a research tool for identification, characterization and purification of interacting G or other signal transduction pathway proteins. Radioactive labels are incorporated into a selected HEDG domain by various methods known in the art and used in vitro to capture interacting molecules. A preferred method involves labeling the primary amino groups in HEDG with $^{125}$I Bolton-Hunter reagent (Bolton, A E and Hunter, W M. (1973) Biochem J 133: 529). This reagent has been used to label various molecules without concomitant loss of biological activity (Hebert C A et al (1991) J Biol. Chem. 266:18989: McColl S et al (1993) J Immunol 150:4550–4555).

Labeled HEDG is useful as a reagent for the purification of molecules with which it interacts. In one embodiment of affinity purification, membrane-bound HEDG is covalently coupled to a chromatography column. Cell-free extract derived from synovial cells or putative target cells is passed over the column, and molecules with appropriate affinity bind to HEDG. HEDG-complex is recovered from the column, and the HEDG-binding ligand disassociated and subjected to N-terminal protein sequencing. This as sequence is then used to identify the captured molecule or to design degenerate oligonucleotide probes for cloning the relevant gene from an appropriate cDNA library.

In an alternate method, antibodies are raised against HEDG, specifically monoclonal antibodies. The monoclonal antibodies are screened to identify those which inhibit the binding of labeled HEDG. These monoclonal antibodies are then used therapeutically.

Example 13

Use and Administration of Antibodies, Inhibitors, or Antagonists

Antibodies, inhibitors, or antagonists of HEDG (or other treatments to limit signal transduction, LST) provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger HEDG activity are treatable with LSTs. These conditions or diseases are specifically diagnosed by the tests discussed above, and such testing should be performed in suspected cases of viral, bacterial or fungal infections: allergic responses; mechanical injury associated with trauma; hereditary diseases; lymphoma or carcinoma; or other conditions which activate the genes of lymphoid or neuronal tissues.

Example 14

Autoimmune Disorders

Autoimmune disorders whereby antibodies are produced against HEDG can be expected to be associated with disease states. For example, for HEDG, such disorders can be expected to be associated with decreased muscle activity that presents much like myasthenia gravis, or to be associated with decreased pain perception. See, for an example of a disease caused by autoantibodies to a molecule involved in neurotransmission (glutamic acid decarboxylase), Nathan et al., J. Neurosci. Res. 40: 134–137, 1995.

The presence of these antibodies can be measured by established immunological methods using protein sequences obtained from the nucleic acids described herein or the related glycine transporters reported elsewhere. See, for example, Kim et al., Mol. Pharmacol., 45: 608–617, 1994 and Liu et al., J. Bio. Chem. 268: 22802–22808, 1992. Such immunological methods are described, for example, in Ausubel et al., Short Protocols in Molecular Biology, John Wiley & Sons, New York, 1992.

Example 15

Production of Transgenic Animals

Animal model systems which elucidate the physiological and behavioral roles of the HEDG receptor are produced by creating transgenic animals in which the activity of the HEDG receptor is either increased or decreased, or the amino acid sequence of the expressed HEDG receptor is altered, by a variety of techniques. Examples of these techniques include, but are not limited to: 1) Insertion of normal or mutant versions of DNA encoding a HEDG receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these HEDG receptor sequences. The technique of homologous recombination is well known in the art. It replaces the native gene with the inserted gene and so is useful for producing an animal that cannot express native HEDG receptors but does express, for example, an inserted mutant HEDG receptor, which has replaced the native HEDG receptor in the animal's genome by recombination, resulting in underexpression of the transporter. Microinjection adds genes to the genome, but does not remove them, and so is useful for producing an animal which expresses its own and added HEDG receptors, resulting in overexpression of the HEDG receptors.

One means available for producing a transgenic animal, with a mouse as an example, is as follows: Female mice are mated, and the resulting fertilized eggs are dissected out of their receptor is cesiumchloride oviducts. The eggs are stored in an appropriate medium such as M2 medium. DNA or cDNA encoding a HEDG purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplary purposes.

All publications and patents mentioned in the above specification are herein incorporated by reference.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

It is claimed:

1. A purified polynucleotide comprising a nucleic acid sequence encoding the polypeptide of SEQ ID NO:2, or the complement of said polynucleotide.

2. The polynucleotide of claim 1 comprising the nucleic acid sequence for (hedg) of SEQ ID NO:1.

3. A composition comprising an oligomer of the polynucleotide of claim 2.

4. An isolated nucleic acid comprising the complement of the polynucleotide of SEQ ID NO: 1.

5. A composition comprising an isolated nucleic acid comprising the complement of the polynucleotide of SEQ ID NO: 1 in a pharmaceutically acceptable excipient.

6. An expression vector comprising a purified polynucleotide comprising a nucleic acid sequence encoding the polypeptide of SEQ ID NO: 2.

7. A host cell transformed with the expression vector of claim 6.

8. A method for producing a polypeptide, said method comprising the steps of:

a) culturing the host cell of claim 7 under conditions suitable for the expression of the polypeptide; and b) recovering the polypeptide from the host cell culture.

* * * * *